United States Patent [19]

Hoskins

[11] Patent Number: 4,678,754
[45] Date of Patent: Jul. 7, 1987

[54] LIQUID CLINICAL CONTROL STANDARD, AND REAGENT PRODUCTS

[75] Inventor: Michael K. Hoskins, Orange, Calif.

[73] Assignee: Ciba Corning Corp., Medfield, Mass.

[21] Appl. No.: 926,467

[22] Filed: Nov. 3, 1986

Related U.S. Application Data

[62] Division of Ser. No. 740,861, Jun. 3, 1985, Pat. No. 4,643,976.

[51] Int. Cl.$^4$ .......................................... G01N 31/00
[52] U.S. Cl. ......................................... 436/15; 436/8; 436/11
[58] Field of Search ...................................... 436/8–19; 252/408.1

[56] References Cited

U.S. PATENT DOCUMENTS 4,116,336 9/1978 Sorensen et al. ..................... 436/11

Primary Examiner—Kyle: Deborah L.
Assistant Examiner—T. J. Wallen
Attorney, Agent, or Firm—B. D. Voyce

[57] ABSTRACT

This invention relates to the field of clinical controls useful for calibrating clinical chemistry analyzers and in manual testing methods, as well as clinical standards and reagents. In addition, it relates to methods for producing stabilized liquid clinical control, standards, and reagents.

3 Claims, 2 Drawing Figures

LIQUID CLINICAL CONTROL STANDARD, AND REAGENT PRODUCTS

This is a division of application Ser. No. 740,861, now U.S. Pat. No. 4,643,976, filed June 3, 1985.

FIELD OF THE INVENTION

This invention relates to the field of clinical controls useful for calibrating clinical chemistry analyzers and in manual testing methods, as well as clinical standards and reagents. In addition, it relates to methods for producing stabilized liquid clinical control, standards, and reagents.

BACKGROUND ART

Chemistry analyzers occupy a preeminent position in the clinical environment, providing significant data regarding the diagnosis and treatment of patient illnesses. Accordingly, there has been a concerted effort by many investigators to develop automated and manual methods for the determination and qualification of constituents in body fluids such as acid phosphatase, alanine aminotransferase, albumin, aldolase, alkaline phosphatase, alpha-hydroxybutyrate dehydrogenase, amylase, aspartate aminotransferase, bicarbonate, direct bilirubin, total bilirubin, blood urea nitrogen, total calcium, carbon dioxide, chloride, total cholesterol, cholinesterase, cortisol, creatine kinase, creatine, digoxin, gamma glutamyl-transferase, globlin, glucose, ldh-cholesterol, iron, lactate dehydrogenase-1, lactate, osmolality, phenylalanine, phosphorus, potassium, salicylate, sodium, T3, T3 uptake, T4, total iron binding capacity, tri glycerides, and uric acid.

Both the manual and automated methods available for each one of the above analytes require either controls or reagents whereby the procedures and other variable parameters of the clinical chemistry analyzers may be checked to ensure accuracy of the testing method or instrument.

Conventional attempts to prolong the stability of chemistry controls and related reagents include reduction of the controls to a dry format which is typically refrigerated at approximately 4° C. Often, the dry format is made by lyophilization rather than spray drying as the former operates at far lower temperatures than the latter. Heat aggravates degradation of analytes and proteins in general and thus, cold processes such as freeze concentration and freeze drying, have been preferred. Although stability in a lyophilized state is enhanced over that associated with the aqueous format, significant losses in constituent activity levels of known chemistry controls are incurred.

One attempt at a freeze-stable liquid blood control standard is disclosed in U.S. Pat. No. 4,199,471 to A. L. Louderback, et al. The standard comprises a sealed receptacle containing specifically treated red cells and a gaseous head space at least equal to about the volume of the red cells. The special treatment comprises thoroughly washing and separating the red cells from the plasma components and mild treatment with aldehyde, slow admixture and lower aliphatic diol or triol, and retention in a buffered solution. The special treatment optionally includes treating at least a portion of the red cells with carbon monoxide. The head space comprises from 0–15% $CO_2$, 0–25% $O_2$ and the balance $N_2$ and/or inert gas.

A different approach to stabilizing liquid clinical controls is disclosed in U.S. Pat. No. 4,121,905 to Jonas Maurukus. Biological reference materials are lyophilized rapidly at $-20°$ to $-30°$ C., then reconstituted in a medium having 20–50% by weight of an alkylene polyol. The claimed stability is 4 to 5 weeks at 2° to 8° C.

DISCLOSURE OF THE INVENTION

The present invention provides a stable liquid clinical chemistry control that can be used either in a multiparameter format or in specific analyte formats. It also provides for clinical chemistry reagents which have improved stability at refrigerated temperatures.

More particularly, the liquid control comprises a storage pouch made with a water and oxygen impermeable material which is at least partially filled with either a clinical chemistry liquid control or reagent and an inert gas. The pouch has a reservoir for holding the liquid, and a filling inlet and a dispensing outlet which are heat-sealed and connected to the reservoir. For the purpose of this specification, the reservoir can have more than one filling inlet and dispensing outlet. Also, the reservoir can have more than one chamber such that the pouch as a whole holds a combination of materials. The chamber contents can be mixed either internally, by rupturing the dividing wall between the chambers, or externally, by having the chambers connected either to separate dispensing outlets or a single dispensing outlet.

The present pouch offers a variety of applications that can be tailored to the user. In one configuration, storable unit-dose liquid controls can be made which do not require remixing and measurement. A stable, ready to use control is available simply by tearing open the dispensing outlet and pouring out the pre-measured contents. Alternatively, the pouch can be filled with multiple doses and be provided with a folding flap at the bottom which permits the pouch to remain upright. Finally, if liquid reagents are used, the pouch can be filled only partially so as to permit additional fluids to be added, perhaps by pipetting, and mixed in the pouch.

MODES OF CARRYING OUT THE INVENTION

The liquid control and reagent products of the present invention are useful for manual and automated methods in chemistry analysis and, in particular, may be used with multichannel chemistry analyzers such as the ACA TM from DuPont or the SMAC TM from Technicon. The liquid control material is a patient-like sample characterized by a range of values for each constituent, enzyme and analyte found therein. The closer the control material simulates a patient's sample in providing all unknowns at their proper levels and in appearance (i.e., optical clarity and the like), the more useful it is. Similarly, the longer it presents such characteristics, i.e., the greater the time period it can hold the activity level for each constituent in a stable fashion, the more valuable the control material.

An example of the liquid control components that can be added are listed as follows:

| CONSTITUENT | UNITS | LEVEL I | LEVEL II | LEVEL III |
| --- | --- | --- | --- | --- |
| ACETOMINOPHEN | mg/l | 10 | 20 | 50 |
| ALBUMIN | g/dl | 4 | 6 | 8 |
| ALK PHOS | U/L | 60 | 100 | 250 |
| ALT | U/L | 30 | 60 | 100 |
| AMYLASE | U | 50 | 100 | 300 |
| AST | U/L | 30 | 60 | 100 |
| DIRECT BILIRUBIN | mg/dl | .25 | — | 2 |
| TOTAL BILIRUBIN | mg/dl | 1 | 2 | 6 |
| CALCIUM | mg/dl | 8 | 10 | 12 |
| CALCIUM, IONIZED | mEq/L | 2 | 2.5 | 4 |
| CARBON DIOXIDE | mEq/L | 10 | 20 | 30 |
| CHLORIDE | mEq/L | 80 | 100 | 120 |
| CHLORAMPHENICOL | ug/ml | 50 | 75 | 100 |
| CHOLESTEROL | mg/dl | 60 | 120 | 240 |
| CREATININE | mg/dl | 1 | 2 | 6 |
| CORTISOL | ug/dl | 50 | 120 | 350 |
| DIGOXIN | ng/ml | 5 | 10 | 35 |
| ETOH | mg/dl | 50 | 100 | 150 |
| GENTAMICIN | ug/ml | 2 | 5 | 10 |
| GLUCOSE | mg/dl | 50 | 110 | 250 |
| GGT | U/L | 25 | 50 | 150 |
| HBDH | U/L | 100 | 200 | 450 |
| HDL CHOLESTEROL | mg/dl | 80 | 100 | 150 |
| IRON | ug/dl | 50 | 100 | 250 |
| LACTIC ACID | mg/dl | 0.5 | 2.0 | 5.0 |
| LD | U/L | 60 | 120 | 350 |
| LIPASE | U | 10 | 25 | 50 |
| LITHIUM | mEq/L | 0 | 1 | 2 |
| MAGNESIUM | mg/dl | 1 | 2 | 4 |
| MAGNESIUM | mg/dl | 1 | 2 | 4 |
| PHOSPHOLIPIDS | mg/dl | 50 | 100 | 200 |
| PHOSPHOROUS | mg/dl | 2.5 | 4 | 8 |
| POTASSIUM | mEg/L | 2.5 | 4.5 | 6 |
| SALICYLATE | mg/dl | 2 | 5 | 10 |
| SODIUM | mEg/L | 120 | 140 | 150 |
| T3 | ng/dl | 50 | 100 | 300 |
| T4 | ug/dl | 2.5 | 7 | 14 |
| TOBRAMYCIN | ug/ml | 10 | 5 | 2 |
| TOTAL LIPIDS | mg/dl | 200 | 400 | 900 |
| TOTAL PROTEIN | g/dl | 4 | 6 | 8 |
| BUN | mg/dl | 10 | 20 | 45 |
| URIC ACID | mg/dl | 3 | 6 | 10 |
| VITAMIN B12 | pg/ml | 50 | 400 | 1000 |

* Both human and animal sources can be used.

As in the above example, preferably the controls and reagents have a combination of anaerobic bacteriacide added.

Figure 1:
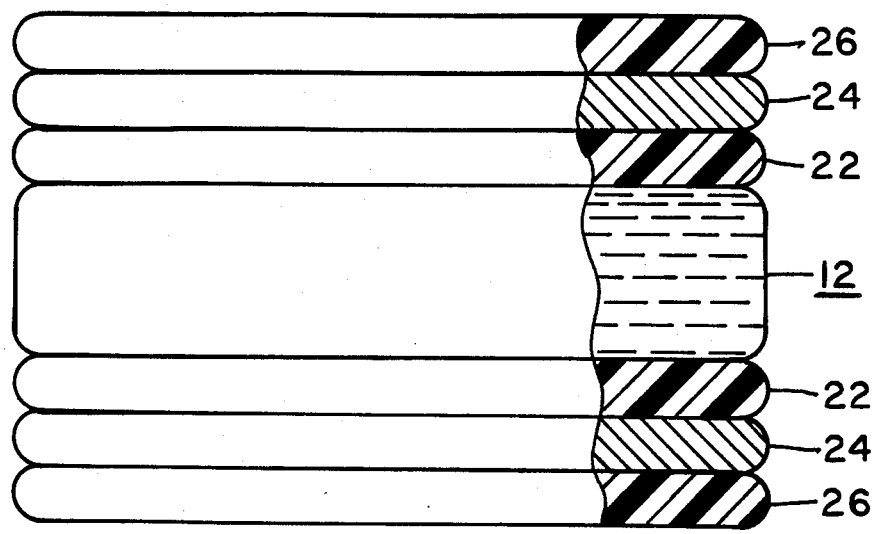
FIG. 1 is an overhead view of the present liquid control.
Figure 2:
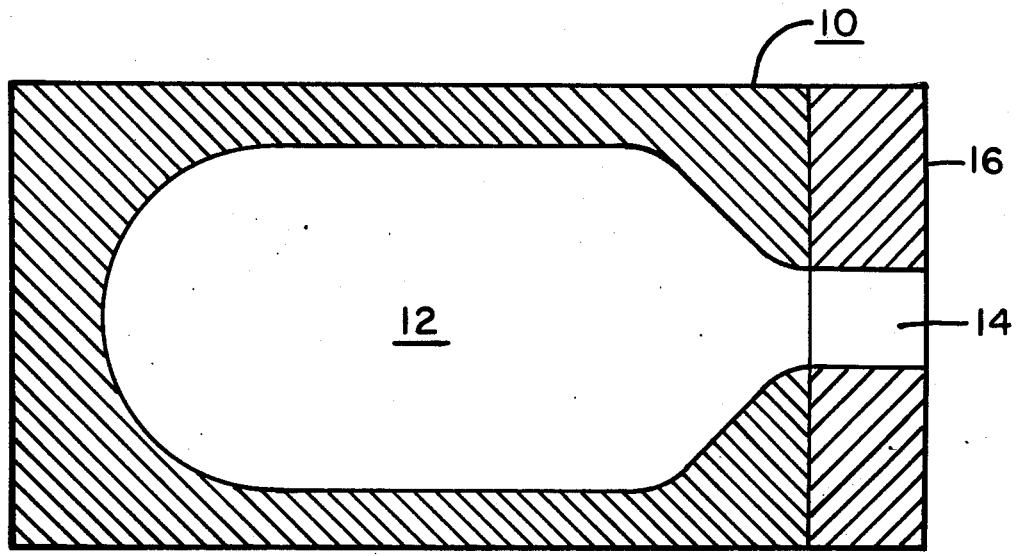
FIG. 2 is a cross sectional view of a portion of the present liquid control.

A preferred embodiment of the claimed control can be described best by reference to FIGS. 1 and 2. The general configuration of the control is a storage pouch 10 having a reservoir 12 with an arcuate bottom designed to contain a single unit-dose of liquid clinical control and a combined filling inlet/dispensing outlet 14. After a combination of inert gas (such as argon, neon, or nitrogen) and control is poured into the reservoir, the end of the inlet/outlet is sealed 16, preferably at ambient pressure.

If a multi-chambered reservoir is desired, the walls of the reservoir can be sealed to form a chamber dividing wall. If heat sealed the chamber will remain separate, however, if cold-roller sealed, then a burstable design is possible whereby one can gently squeeze the pouch, rupture the dividing wall, and thus mix the contents of the separate chambers.

The flexible pouch is made of a three layer laminate 20. The inner layer 22, which surrounds the reservoir 12, is made of a heat sealable water barrier, inert to the control liquid. A suitable material would be 1 mil polyethylene film. The middle layer 24 is an oxygen barrier, preferably 2 mil aluminum foil. The outer laminate layer is a puncture-resistant protection barrier that stands up to the physical stresses of transport and storage in bulk. A suitable material for this is 1 mil polyester film. The laminate can be formed by conventional means such as reverse gravure printing. Equivalent substitute materials would be known to the art.

The benefits in using the present pouch packaging for liquid controls and reagents are unexpected for several reasons. First, many of the biological components in controls and reagents are highly susceptible to denaturation and degradation at elevated temperatures, especially the 350° F. level needed to heat seal the above laminate. However, by adding the control and an inert gas under pressure substantially at the same time, the control is never exposed to temperatures above 40° C. Also, the inert gas drives out ambient $O_2$ such that dissolved $pO_2$ sample levels drop from 160 to 10–20 torr. Unlike oxygen permeable containers, the present pouch does not allow easy oxygen mixing, and thus, components such as bilirubin, uric acid and sulfhydryl enzymes, which would oxidize readily a clinical pHO (7.4) are stable for long periods of time.

The elimination of any light transmitted to the contents of the pouch prevents photo-chemical processes from degrading any of the analytes which are present in the formulation.

EXAMPLE 1

A useful clinical chemistry control combines a series of analytes together in such a way that the sum of the analytes mimic a patient's specimen under ordinary laboratory conditions. Each of these individual analytes are measurable by any number of chemical, electrical, and immunological methods. Therefore, with an increasing number of analytes in a particular control material, one would expect increasing interferences with many of these methods. Whole human serum, the liquid portion of the blood separated from the clot, is the sample of choice for many of the routine chemistry tests run in the hospital laboratory. The analytes which have clinical significance in this serum are generally stable for use within a one-day period after the serum has been separated from the red blood cells. These analytes degrade with time by a series of destructive mechanisms, i.e., heat, oxidation, light. Thus, ordinary human serum of defribrinated plasma is unsuitable as a base material for a liquid control.

In order to ensure that all analytes are stable, it is necessary that the base protein be free of most of the unstable analytes targeted for use in the control. It has been useful for us to start with a base of either fraction 5 albumin or serum which has been "stripped" of any of these labile components. In the case of albumin solutions, a buffer is added to control the pH of the control material during the stability period. A series of antimicrobial agents are added to minimize the growth of microorganisms in the control medium. To this matrix, analytes are added as stabilized materials to this stabilized matrix—each designed to minimize interactions with other analytes. For example LDH is added as a purified preparation from chicken heart which is far more stable than normal serum LDH.

To minimize the oxidation of all components which are added to the control, the matrix is maintained at a very low level of dissolved oxygen during the preparation and filling of the control. This is accomplished by maintaining an inert gas presence in intimate contact with the product during processing.

The presence of the inert gas and the exclusion of additional oxygen due to the composition of the pouch, minimizes the changes in analyte values during any subsequent freezing and thawing of the material. Under ordinary conditions many analytes lose significant activity if they are frozen and thawed.

EXAMPLE 2

It is useful, both in the doctor's office and the hospital laboratory, to have a calibrator to verify the effectiveness of the urine "dipsticks" which are used routinely in urinalysis. A liquid control material has been formulated where the constituents which are analyzed using current dipstick methods are added to a stabilized human urine preparation. The present pouch is filled with this preparation in the presence of argon. The pouch has suitable dimensions for inserting a dipstick directly into the pouch to come into contact with the control material. This single-use control concept would be eminently suitable for a doctor's office as well as a large hospital laboratory.

EXAMPLE 3

The present pouch has been designed with multiple compartments to contain reagents which would be incompatible for extended storage periods. These compartments would be separated by a heat seal which could be ruptured, causing the two reagents to mix in a single compartment of the pouch. A patient's sample could be added to the contents of the pouch by means of pipetting, and the entire contents of the pouch aspirated into a spectrophotometer or other instrument to quantitate the analyte being measured.

The final result is an unexpected long stability period. At refrigerated temperatures of 5°–8° C., controls and reagents are stable for 2–8 months, whereas when frozen at $-10°$ C., the stability shown by present data supports predictions of stability from 3 to 5 years.

What is claimed is:

1. A process for making stable clinical protein-based liquid solutions comprising simultaneously filling a storage pouch, having a reservoir and connected to the reservoir at least one heat-sealed filling inlet and at least one heat-sealed dispensing outlet, with a clinical protein-based liquid having a temperature below its denaturation point and an inert gas having a temperature below ambient temperature which is sufficient to cool either the liquid or the pouch such that the heat sealing of the inlet and the outlet does not substantially denature the clinical proteins in the liquid.

2. The process of claim 1 wherein the filling inlet of the pouch also serves as the dispensing outlet.

3. The process of claim 2 wherein the pouch is made of a laminate comprising:
 (a) an inner layer which is heat sealable, a water barrier, and inert with respect to the control liquid;
 (b) a middle layer which is an oxygen barrier; and
 (c) an outer layer which is a puncture-resistant protection barrier.

* * * * *